Dec. 15, 1959 E. S. BOERNER Plant Pat. 1,889
CHRYSANTHEMUM PLANT
Filed March 10, 1959
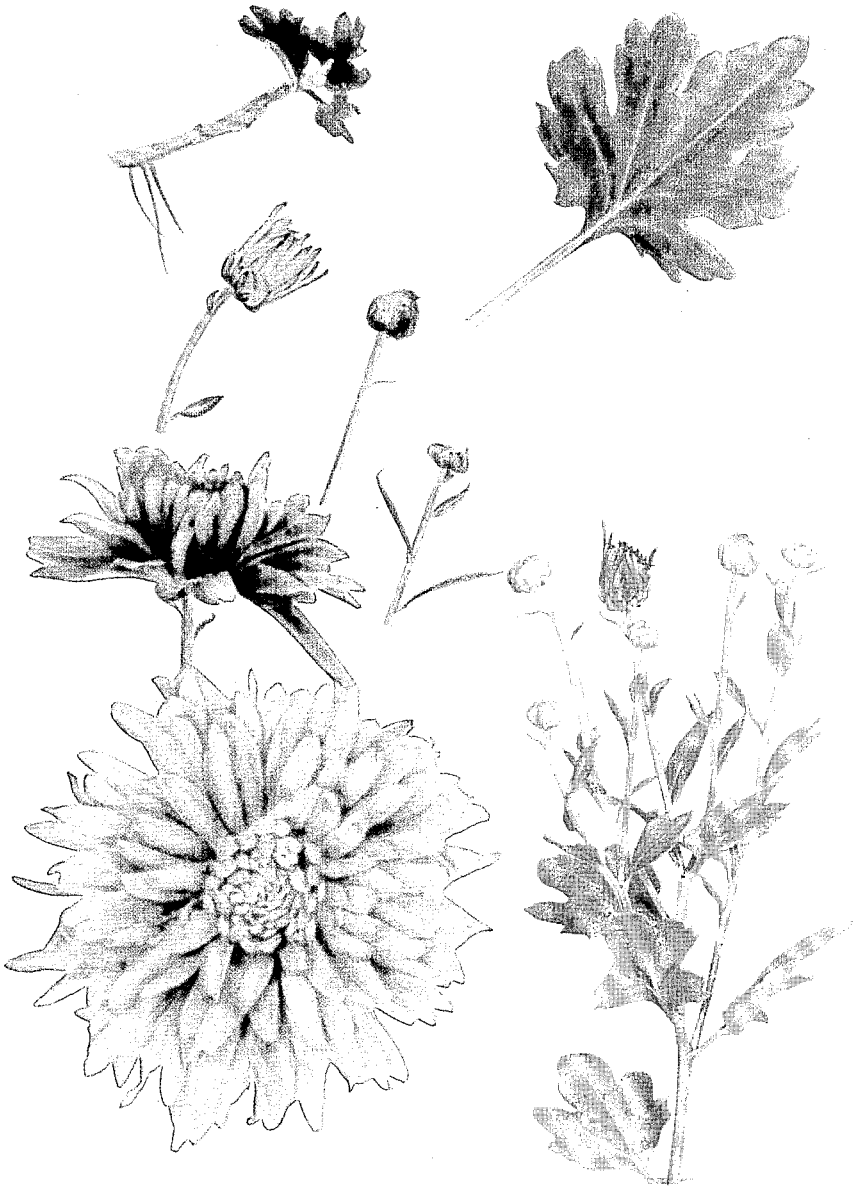
Inventor.
E. S. Boerner
By: Robb & Robb
Attorneys.

United States Patent Office

Plant Pat. 1,889
Patented Dec. 15, 1959

1,889

CHRYSANTHEMUM PLANT

Eugene S. Boerner, Newark, N.Y., assignor to Jackson & Perkins Company, Newark, N.Y., a corporation of New York Application March 10, 1959, Serial No. 798,570

1 Claim. (Cl. 47—60)

The present invention relates to a new and distinct variety of chrysanthemum plant of the decorative type, which was originated by me by crossing an unnamed and unpatented seedling derived from a cross of "Chippewa" (unpatented) × "Tanager" (Plant Patent No. 1,129) with the variety "Tanager."

The primary objective of this breeding was to produce a new variety of chrysanthemum of good hardiness, bearing flowers of Spectrum Red general color tonality. This objective was fully achieved, along with other improvements, as evidenced by the following unique combination of characteristics which are outstanding in the new variety and which distinguish it from its parents as well as from all other varieties of which I am aware:

(1) A low, compact habit of growth;

(2) A distinctive Spectrum Red general color tonality of the flowers;

(3) An early blooming habit, which is unusual for a chrysanthemum of this color; and (4) A hardiness which is also unusual in a chrysanthemum of this color.

A sexual reproduction of my new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black-and-white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, near mid-morning in the latter part of September:

Parentage: An unnamed seedling of "Chippewa" × "Tanager" × "Tanager."

Classification: Decorative.

Growth: Low; compact.

Cold resistance: The plant is winter hardy in northern New York, but the flowers show slight frost-burn with early frost.

Blooming period: In the Newark, New York climatic area, average period of bloom runs from early September until frost.

*Flower*

Bud:

*Color.*—When sepals first divide—Tyrian Rose, Plate 12. When petals begin to unfurl—Spinel Red, Plate 26. When half-blown: inside of petals—Carmine, Plate 1; outside of petals—Pomegranate Purple, Plate 12.

*Peduncle.* — Color — Grape Green, Plate 41. Strength—strong.

Bloom:

*Size.*—4½ inches.

*Stem.*—Strong.

*Form.*—Decorative.

*Petalage.*—Double.

*Color.*—Center of flower—Scarlet Red, Plate 1. Outer petals—Spectrum Red, Plate 1. Base of petals—Deep Sea-foam Green, Plate 31. Inside of petals—Spectrum Red, Plate 1, lightly overcast with Carmine, Plate 1. Reverse of petals—Pomegranate Purple, Plate 12.

*Petals.*—Texture—medium. Form—oval.

*Fragrance.*—Characteristic chrysanthemum.

*Plant*

Form: Low; compact.

Growth: Free.

Foliage:

*Size.*—Medium.

*Quantity.*—Normal.

*Color.*—Upper side—Chromium Green, Plate 32. Under side—Light Hellebore Green, Plate 17.

*Texture.*—Leathery.

I claim:

A new and distinct variety of chrysanthemum plant of the decorative type, substantially as herein shown and described, characterized particularly as to novelty by the unique combination of a low and compact habit of growth, a distinctive Spectrum Red general color tonality of the flowers, an early blooming habit, and good hardiness.

No references cited.